United States Patent
Zweigart et al.

(10) Patent No.: US 8,435,751 B2
(45) Date of Patent: *May 7, 2013

(54) MEMBRANE FOR CELL EXPANSION

(75) Inventors: Carina Zweigart, Shomberg (DE);
Bernd Krause, Rangendingen (DE);
Markus Neubauer, Balingen (DE);
Reinhold Deppisch, Hechingen (DE);
Doris Deppisch, legal representative, Hechingen (DE)

(73) Assignee: Gambro Lundia AB, Lund (SE)

( * ) Notice: Subject to any disclaimer, the term of this patent is extended or adjusted under 35 U.S.C. 154(b) by 86 days.

This patent is subject to a terminal disclaimer.

(21) Appl. No.: 13/120,397

(22) PCT Filed: Sep. 23, 2009

(86) PCT No.: PCT/EP2009/006849
§ 371 (c)(1),
(2), (4) Date: Apr. 27, 2011

(87) PCT Pub. No.: WO2010/034468
PCT Pub. Date: Apr. 1, 2010

(65) Prior Publication Data
US 2011/0263020 A1  Oct. 27, 2011

(30) Foreign Application Priority Data

Sep. 25, 2008 (EP) .................................. 08016810

(51) Int. Cl.
*G01N 33/53*  (2006.01)

(52) U.S. Cl.
USPC ........... 435/7.21; 435/378; 435/396; 210/640

(58) Field of Classification Search ................. 435/7.21, 435/378, 396; 210/640
See application file for complete search history.

(56) References Cited

U.S. PATENT DOCUMENTS 4,056,467 A  11/1977  Christen et al.
4,749,619 A   6/1988  Angleraud
(Continued)

FOREIGN PATENT DOCUMENTS

EP  0362588      11/1990
EP  0 550 798 A1  7/1993
(Continued)

OTHER PUBLICATIONS

Humes et al., 1999, "Replacement of Renal Function in Uremic Animals with a Tissue-Engineered kidney", Nature Biotechnology, 17, 451-455.

(Continued)

*Primary Examiner* — Peter D. Mulcahy
*Assistant Examiner* — Henry Hu
(74) *Attorney, Agent, or Firm* — Barnes & Thornburg LLP

(57) ABSTRACT

A membrane which can be used for cultivating cells, in particular adherent cells. The membrane permits the adhesion and proliferation of the cells based on its specific composition comprising polyurethane. The resulting surface characteristics further permit the membrane to be used without any pre-treatment with surface modifying substances. A method for preparing a membrane which can be used for cultivating cells, in particular adherent cells. Methods of using the membrane for cultivating cells, in particular adherent cells.

11 Claims, 8 Drawing Sheets

U.S. PATENT DOCUMENTS

| | | | |
|---|---|---|---|
| 4,935,141 | A | 6/1990 | Buck et al. |
| 5,151,227 | A | 9/1992 | Nguyen et al. |
| 5,369,012 | A | 11/1994 | Koontz et al. |
| 5,431,817 | A * | 7/1995 | Braatz et al. .............. 210/490 |
| 5,686,289 | A | 11/1997 | Humes et al. |
| 5,891,338 | A | 4/1999 | Bell et al. |
| 5,954,966 | A * | 9/1999 | Matsuura et al. .......... 210/640 |
| 6,103,117 | A | 8/2000 | Shimagaki et al. |
| 6,150,164 | A | 11/2000 | Humes |
| 6,942,879 | B2 | 9/2005 | Humes |
| 6,960,297 | B2 | 11/2005 | Kozawa et al. |
| 7,470,368 | B2 | 12/2008 | Sugaya et al. |
| 7,837,042 | B2 | 11/2010 | Yokota et al. |
| 2003/0021826 | A1 | 1/2003 | Crost et al. |
| 2003/0203478 | A1 | 10/2003 | Cadwell |
| 2004/0062809 | A1 | 4/2004 | Honiger et al. |
| 2005/0238687 | A1 | 10/2005 | Humes |
| 2005/0274665 | A1 | 12/2005 | Hellmann et al. |
| 2006/0191844 | A1 | 8/2006 | Mahuchi et al. |
| 2006/0234582 | A1 | 10/2006 | Gohl et al. |
| 2007/0082393 | A1 | 4/2007 | Lodhi et al. |
| 2007/0269489 | A1 | 11/2007 | Humes |
| 2010/0016778 | A1 * | 1/2010 | Chattopadhyay ........... 604/6.09 |
| 2010/0326915 | A2 * | 2/2010 | Fislage et al. ............... 210/646 |
| 2010/0163488 | A1 * | 7/2010 | Fislage et al. ............... 210/646 |
| 2011/0263022 | A1 * | 10/2011 | Krause et al. ............... 435/401 |
| 2012/0028275 | A1 * | 2/2012 | Kieferle et al. ............. 435/7.21 |

FOREIGN PATENT DOCUMENTS

| | | |
|---|---|---|
| EP | 0 925 826 A1 | 6/1999 |
| EP | 1 439 212 A1 | 7/2004 |
| EP | 1 875 957 A1 | 7/2006 |
| EP | 1 795 254 A1 | 6/2007 |
| EP | 2 133 298 A1 | 4/2009 |
| EP | 2 113 298 A9 | 11/2009 |
| EP | 1 578 521 B1 | 8/2010 |
| JP | 2003-245526 A | 9/2003 |
| JP | 2004305840 A | 11/2004 |
| WO | 89/01967 A1 | 3/1989 |
| WO | WO90/11820 | 10/1990 |
| WO | WO93/00439 | 1/1993 |
| WO | 01/54802 A1 | 8/2001 |
| WO | 01/56549 A1 | 8/2001 |
| WO | 02/00775 A1 | 1/2002 |
| WO | 2004/056459 A1 | 7/2004 |
| WO | 2004/056460 A1 | 7/2004 |
| WO | 2005/021139 A1 | 3/2005 |
| WO | 2006/135966 A1 | 12/2006 |
| WO | 2006/138537 A2 | 12/2006 |
| WO | 2007/148147 A1 | 12/2007 |
| WO | WO2008/046779 | 4/2008 |
| WO | 2010/034466 A1 | 4/2010 |
| WO | 2010/034468 A1 | 4/2010 |
| WO | 2010/034469 A1 | 4/2010 |
| WO | 2010/034475 A1 | 4/2010 |
| WO | WO2010/034466 | 4/2010 |
| WO | WO2010/034469 | 4/2010 |
| WO | WO2010/034475 | 4/2010 |

OTHER PUBLICATIONS

International Search Report/Written Opinion for PCT/EP2009/006849, completed Nov. 2, 2009.

Aebischer et al., "Renal Epithelial Cells Grown on Semipermeable Hollow Fibers as a Potential Ultrafiltrate Processor", vol. XXXiii Trans Am Soc Artif Intern Organs, 1987, pp. 96-102.

Aebischer et al., "The Bioartificial Kidney: Progress towards an Ultrafiltration Device with Renal Epithelial Cells processing", Life Support Systems (1987), 5, 159-168.

Andrade et al., "Surface Characterization of Poly(Hydroxyethyl Methacrylate) and Related Polymers. I. Contact Angle Methods in Water", Journal of Polymer Science: Polymer Symposium 66, 313-336 (1979).

Anthony Atala, "Recent developments in tissue engineering and regenerative medicine", Current Opinion in Pediatrics, 2008, 18:167-171.

Baer et al., "Isolation of proximal and distal tubule cells from human kidney by immunomagnetic separation", Kidney International, vol. 52 (1997), pp. 1321-1331.

Fey-Lamprecht et al., "Functionality of MDCK kidney tubular cells on flat polymer membranes for biohybrid kidney", Journal of Materials Science: Materials in Medicine 9 (1998) 711-715.

William H. Fissell, "Developments towards an artificial kidney", Future Drugs Ltd., 2006, 155-165.

Green et al., "Measurement of the Transmittance Coefficient Spectrum of Cuprophan and RP69 Membranes: Applications to Middle Molecule Removal via Ultrafiltration", vol. XXII Trans. Amer. Soc. Artif. Int. Organs, 1976, pp. 627-636.

Humes et al., "The bioartificial kidney in the treatment of acute renal failure", Kidney International, vol. 61, Supplement 80 (2002), pp. S121-S125.

Humes et al., "Tissue engineering of a bioartificial renal tubule assist device: IN vitro transport and metabolic characteristics", Kidney International, vol. 55 (1999), pp. 2502-2514.

Akira Saito, "Research into the development of a Wearable Bioartificial Kidney with a Continuous Hemofilter and a Bioartificial Tubule Device Using Tubular Epithelial Cells", Artificial Organs, 28(1):58-63, 2004.

Saito et al., "Present Status and Perspective of the Development of a Bioartificial Kidney for Chronic Renal Failure Patients", Therapeutic Apheresis and Dialysis, 10(4):342-347, 2006.

Sciarratta et al., "Plasma functionalization of polypropylene with acrylic acid", Surface and Coatings Technology 174-175- (2003) 805-810.

International search report from PCT/EP2009/006847 completed Nov. 24, 2009, 10 pages.

International search report from PCT/EP2009/006850 completed Jan. 5, 2010, 9 pages.

International search report from PCT/EP2009/006860 completed Dec. 4, 2009, 10 pages.

* cited by examiner

MEMBRANE FOR CELL EXPANSION

CROSS-REFERENCE TO RELATED APPLICATIONS

This application is the U.S. national phase of PCT/EP2009/006849 filed Sep. 23, 2009. PCT/EP2009/006849 claims priority to European patent application 08016810.7 filed Sep. 25, 2008. The disclosures of both European patent application 08016810.7 and PCT/EP2009/006849 are hereby incorporated herein by reference.

TECHNICAL FIELD

The invention relates to a membrane which can be used for cultivating cells, in particular adherent cells, wherein said membrane allows for the adhesion and proliferation of the cells based on its specific composition comprising polyurethane and the resulting surface characteristics further allow the membrane to be used without any pre-treatment with surface modifying substances. The invention further relates to a method for preparing a membrane which can be used for cultivating cells, in particular adherent cells, and to methods of using such membrane for cultivating cells, in particular adherent cells.

BACKGROUND OF THE INVENTION

The invention particularly relates to membranes which can, for example, be used for culturing adherent cells of various types. Like most cells in vivo, many cells are adherent cells, or anchorage-dependent cells; that is, they can metabolize and divide only if they are attached to a surface or substratum. Only cells of the circulatory system (e.g., lymphocytes and red blood cells) grow unattached and suspended in solution in vitro. While many anchorage-dependent cells may grow on glass or synthetic surfaces, these cells often lose their ability to differentiate and respond to hormones. The loss of cellular morphology not only entails a loss of function, but also prevents regenerative power in a longer-term culture system. Longer-term cultivation would however be of great significance, for example, with the use of human cells for tissue culture, and many cells are not available in any quantity. For this reason, such tissue culture dishes are often coated with extracellular matrix components such as collagen or fibronectin. However, the use of xenogenic factors is a clear disadvantage, especially if the cells as such or on a matrix as used for medical treatment of human beings, as it will bring along risks of contamination and may result in adverse reactions in the patient treated.

The failure of cells to grow on such surfaces or keep their abilities is, for example, a major limitation of current tissue culture techniques. Tissue cultures are a potential source of tissues and organs which could be used for transplantation into humans. For example, tissue cultured skin cells could potentially be used in skin grafts. The aim is to develop biological substitutes that can restore and maintain normal function, for example, by the use of acellular matrices, which will depend on the body's ability to regenerate for proper orientation and direction of new tissue growth, or by the use of matrices or membranes with cells adhered thereto (Atala (2006): Recent developments in tissue engineering and regenerative medicine. Curr. Opin. Pediatr. 16, 167-171). Cells can also be used for therapy via injection, either with carriers or alone. In such cases, the cells need to be expanded in culture, attached to a support matrix, and then reimplanted into the host after expansion. Veterinary therapeutic applications are available today and may represent an additional application of membranes for cell cultivation.

The ability to culture cells, especially adherent cells, is important also because they represent biological "factories" capable of producing large quantities of bio products such as growth factors, antibodies and viruses. These products can then be isolated from the cell cultures and used, for example, to treat human diseases.

Cell cultures also are emerging tools for biocompatibility and toxicology studies in the field of pharmaceutical and life science industry.

Finally, tissue cultures usually comprise cells from only one or a few tissues or organs. Consequently, cell cultures provide scientists with a system for studying the properties of individual cell types without the complications of working with the entire organism.

A known method for adherent cell cultures involves a hollow fiber membrane bioreactor. In this system, the cells are generally attached to the lumen of a cylindrical hollow fiber membrane. Culture media and oxygen flow through the hollow fiber membrane. The molecular weight cut-off of the membrane permits nutrients and oxygen to reach the cells without allowing the cells to escape.

A variety of polymers has been suggested for producing semipermeable membranes for cell and tissue culture (US 2007/269489 A). They include polyalginate, polyvinylchloride, polyvinylidene fluoride, polyurethane isocyanate, cellulose acetate, cellulose diacetate, cellulose triacetate, cellulose nitrate, polysulfone, polyethersulfone, polystyrene, polyurethane, polyvinyl alcohol, polyacrylonitrile, polyamide, polymethylmethacrylate, polytetrafluoroethylene, polyethylene oxide and combinations of such polymers. The polymeric support may also consist of polyethylene terephthalate (PET) or polycarbonate. Further materials which were suggested, for example, as scaffolds for transplantable tissue material, are cellulose, macroporous collagen carriers, or biodegradable matrices.

EP 0 362 588 A1 describes the preparation of membranes which provide for a high concentration of immobilization sites for cells or other bioactive ingredients. The membranes disclosed can be flat or hollow fiber membranes. They are polysulfone (PSf)-based membranes and may further comprise, for example, polyethylene glycol, polyvinylpyrrolidone (PVP) or various polyurethane (PU) pre-polymers. Membranes specifically disclosed are made from polysulfone (Udel™ 3500) in concentrations of at least 8-35% in the casting solution and PVP, or polysulfone and an isocyanate-capped polyurethane prepolymer (BIOPOL™) in concentrations from 6% to 11% in the casting solution. The reference does not give any data on the actual possibility to use the membrane for supporting a cell culture of adherent cells.

WO 93/00439 A1 describes maintaining a cell culture within a biocompatible, semipermeable membrane in which the cells are stimulated and secrete active factor. The semipermeable membrane used permits the diffusion of the active factor therethrough while excluding detrimental agents present in the external environment from gaining access to the culture. The membrane described has a tubular shape and is said to enable the diffusion of molecules having a molecular weight of up to 150 kDa. Suggested materials for said membranes are acrylic copolymers, polyvinylchloride, polystyrene, polyurethane, polyamide, polymethacrylate, polysulfone, polyacrylate, polyvinylidene fluoride, polyurethaneisocyanate, polyalginate, cellulose acetate, polysulfone, polyvinyl alcohols, polyacrylonitrile, polyethylene oxide, and derivatives, and mixtures thereof. The membrane does not, as such, have to serve as a matrix for cell adhesion in this disclosure.

WO 90/11820 A2 discloses flat membranes with surfaces usable for cell growth in vitro or, as an artificial implant, in vivo. The membrane is described as being porous with a pore size in the range of from 0.1 to 100 microns and having a finger-like configuration in an intermediate layer. The membrane comprises a hydrophobic polymer and a hydrophilic polymer. Examples given for the hydrophobic polymer are polyurethane, polyether urethane, polyurethane urea, polyether urethane urea, polyvinylidene fluorides, polyvinyl fluoride, polysulfone, polyamides, polyethersulfone, polyesters, polycarbonates, preferably polyether urethane, and copolymers thereof. Examples given for the hydrophilic polymer are polyacrylic (or methacrylic) acids and co-, ter- and tetrapolymers, polyacrylic (or methacrylic) esters, polyacrylic (or methacrylic) salts, polyhydroxyethyl (or propyl) acrylate (or methacrylate) or hydroxypropyl or trishydroxypropyl acrylamide and co-, ter- and tetrapolymers, polydimethyl (or diethyl) amino ethyl acrylate (or methacrylate or amino propylmethacrylamide) and co-, ter- and tetrapolymers, polyacrylamide (or N-hydroxymethyl) acrylamide and co-, ter- and tetrapolymers, polyvinylpyrrolidone and co-, ter- and tetrapolymers, carboxymethyl cellulose and hydroxyethyl (or hydroxypropyl) cellulose. The reference specifically discloses a membrane made from polyether urethane and a copolymer of acrylic acid and ethyl hexyl methacrylate. The reference does not report whether or not it can be used for adhering and culturing cells.

U.S. Pat. No. 5,431,817 generically discloses membranes comprising as components polysulfone, polyethersulfone or polyestersulfone in an amount of at least from 8% to 35% of the casting solution, optionally further polymers such as PEG or PVP, and isocyanate end-capped polyurethane prepolymers in an amount of from 1% to 20% of the casting solution.

Membranes which are specifically disclosed are made from a polysulfone, a polyurethane prepolymer and PEG. The reference is silent on the ability of the membrane to be used as a matrix for the adherence and culturing of cells.

U.S. Pat. No. 5,151,227 also generically discloses membranes comprising as components polysulfone, polyethersulfone or polyestersulfone in an amount of at least from 8% to 35% of the casting solution, optionally further polymers such as PEG or PVP, and isocyanate end-capped polyurethane prepolymers. However, only membranes comprising polysulfone and PVP are specifically disclosed.

None of the references specifically discloses a membrane comprising, as a first component, polysulfone, polyethersulfone or polyarylethersulfone, PVP as a second component, and polyurethane as a third component. None of the references shows that the membranes disclosed therein can serve as a matrix for culturing adherent cells.

Apart from the problem of identifying membranes which could be used as a matrix for the cultivation of adherent cells, membranes currently known in the art suffer from their inability to sufficiently promote and sustain adherence, expansion, differentiation and extended life-span without the pre-treatment of said membranes or matrices, or the addition of exogenous factors, such as, for example, fibronectin, laminin or collagen.

For example, Fissell (2006) in *Expert Rev. Med. Devices* 3(2), 155, reviews efforts with regard to developing an artificial kidney based on adhering renal tubule cells to a synthetic polysulfone-based hollow-fiber membrane. In this case the membrane has to be coated with ProNectin-L™ in order to promote attachment of the cells.

U.S. Pat. No. 6,150,164 and U.S. Pat. No. 6,942,879 both present elaborate ways towards a bioartificial kidney based on renal cells such as, for example, endothelial cells or so-called renal stem cells, which are seeded into hollow fibers. Hollow fiber membranes which are mentioned as being useful are based on cellulose, polyacrylonitrile, polysulfone and other components or copolymers thereof. The internal and external surface of the hollow fiber is pre-coated with suitable extracellular matrix components (EMC) including Type I collagen, Type IV collagen, laminin, Matrigel, proteoglycan, fibronectin and combinations thereof. Only after such treatment the cells can be seeded.

SUMMARY OF THE INVENTION

The present invention provides membranes which are defined by a novel combination of polymeric components comprising, as a first polymer component, polysulfone, polyethersulfone or polyarylethersulfone, as a second polymer component polyvinylpyrrolidone, and as a third polymer component polyurethane. The present invention is also directed to a method of preparing such membranes. The present invention is also directed to methods of using the membranes for promoting cell attachment and the cultivation of cells, in particular adherent cells, with high performance characteristics without having to pre-treat or pre-coat the membranes with any extracellular matrix components.

BRIEF DESCRIPTION OF THE DRAWINGS

FIG. 1 (B) is a scanning electron micrograph of the cell-contacting surface of the membrane with a magnification of 40,000×. The white bar indicates 800 nm.

FIG. 2 (B) is a scanning electron micrograph of the inner surface of the membrane (magnification 60,000×), which is very smooth. This surface is the contact site for cells. The white arrow indicates 500 nm.

Figure 3:
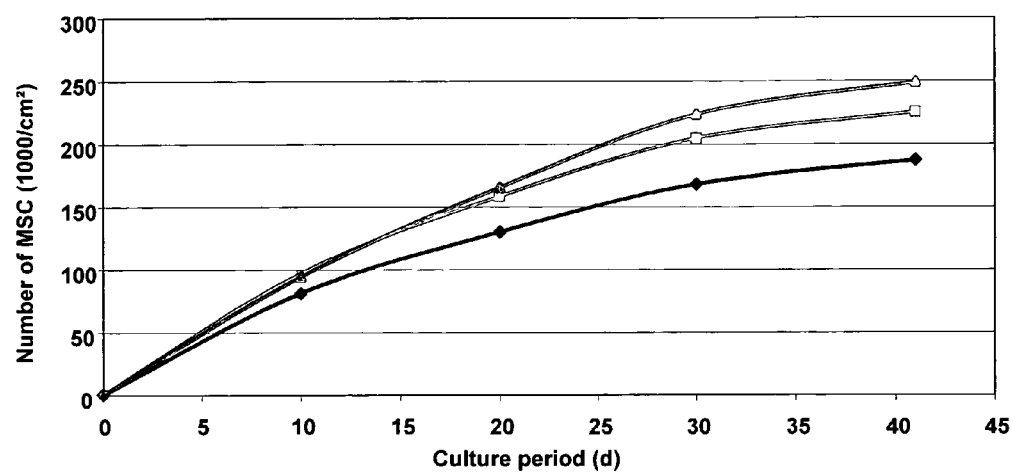
FIG. 3 shows a long-term culture of mesenchymal stem cells (MSC) on flat sheet membranes prepared from a polymer solution comprising 0.5 wt.-% polyurethane (-■-) and 2.0 wt.-% polyurethane (-▲-), respectively, in comparison to a standard tissue culture polystyrene (TCPS) matrix (-♦-) over a culture period of 40 days. Depicted are the numbers of MSC in 1,000/cm$^2$.
Figure 4:
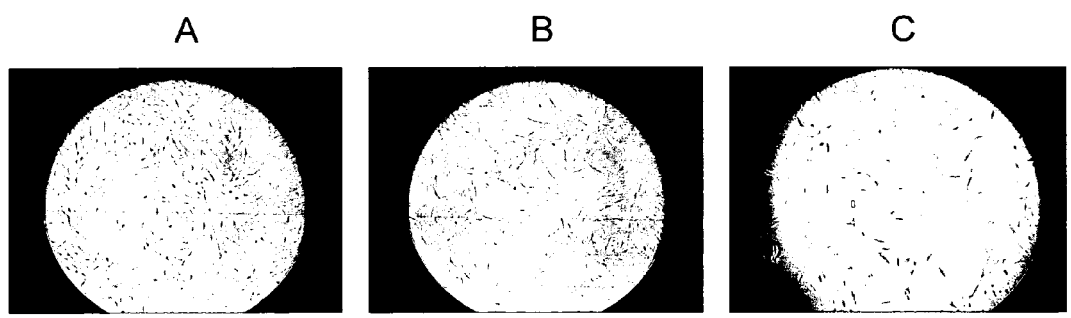
FIG. 4 shows the morphology of MSC after replating the cells on TCPS following their cultivation on flat sheet membranes as shown in FIG. 3. Figure (A) shows cells which have been grown on the standard TCPS matrix. Figure (B) shows cells which have been grown on a flat sheet membrane based on a polymer solution comprising 0.5 wt.-% polyurethane. Figure (C) shows cells which have been grown on a flat sheet membrane based on a polymer solution comprising 2.0 wt.-% polyurethane. The morphology of the cells grown on the polyurethane containing membranes is comparable to the standard TCPS.
Figure 5:
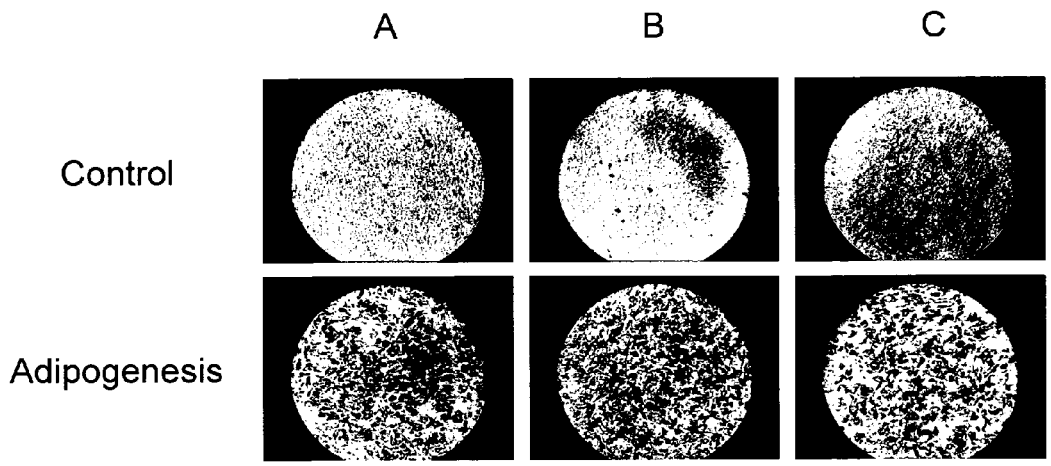

FIG. 5 shows the ability of MSC cultivated on flat sheet membranes as shown in FIG. 3 to differentiate into adipocytes. The cells grown on membranes based on polymer solutions comprising 0.5 wt.-% polyurethane (B) and 2.0 wt.-% polyurethane (C), respectively, were fully able to differentiate to adipocytes, also in comparison with those cultivated on a standard TCPS matrix (A). Pictures in the upper row represent control cells, i.e. cells not hormonally induced in order to differentiate into the adipogenic lineage but cultured in standard culture medium. Pictures in the lower row represent differentiated cells after exposure to an adipogenic induction cocktail.

Figure 6:
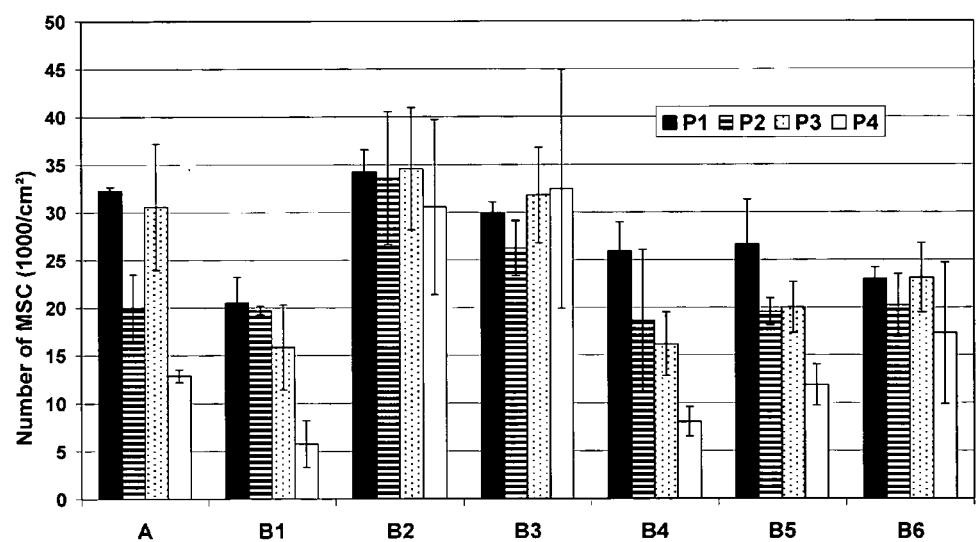

FIG. 6 depicts results of a long-term culture over four passages of MSC on PU containing flat sheet membranes (B1-B6) of the invention in comparison with a standard polystyrene culture matrix (A). Membranes B1 to B6 are based on different amounts of polyurethane in the polymer solution (B1: 2 wt.-%; B2: 0.5 wt.-%; B3: 0.2 wt.-%; B4: 0.1 wt.-%; B5: 0.05 wt.-%; B6: 0.01 wt.-%). The caption shows the respective number of passages which the cells have undergone. In comparison with Tissue Culture Polystyrene as the standard material of culture flasks for MSC expansion, all membranes according to the invention exhibit an equally well performance with respect to MSC expansion over four passages.

Figure 7:
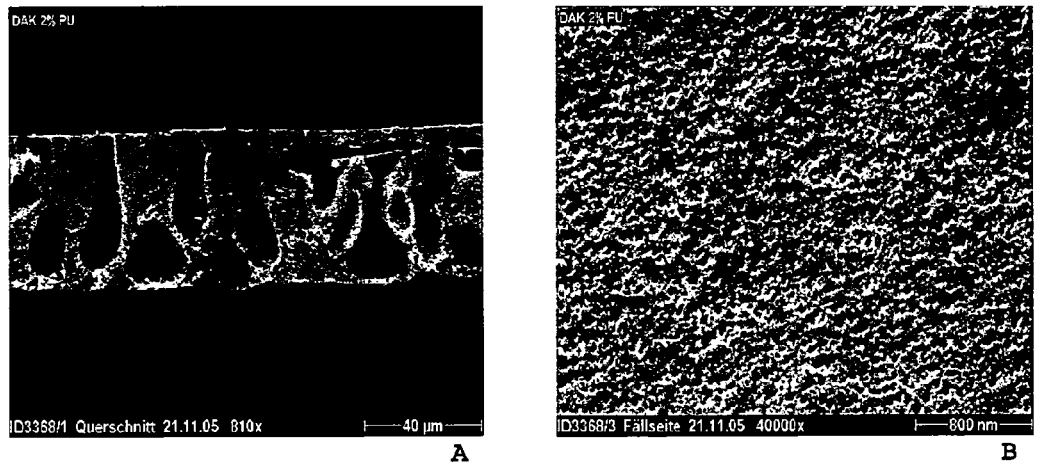

FIG. 7 shows a scanning electron micrograph (SEM) of the cross-section of the flat sheet membrane (A) prepared in Example 1. Magnification: 810×. The white bar indicates 40 µm. Also shown is the surface of the membrane (precipitated (non-glass) side) (B). Magnification 40,000×. The white bar indicates 800 nm.

Figure 8:
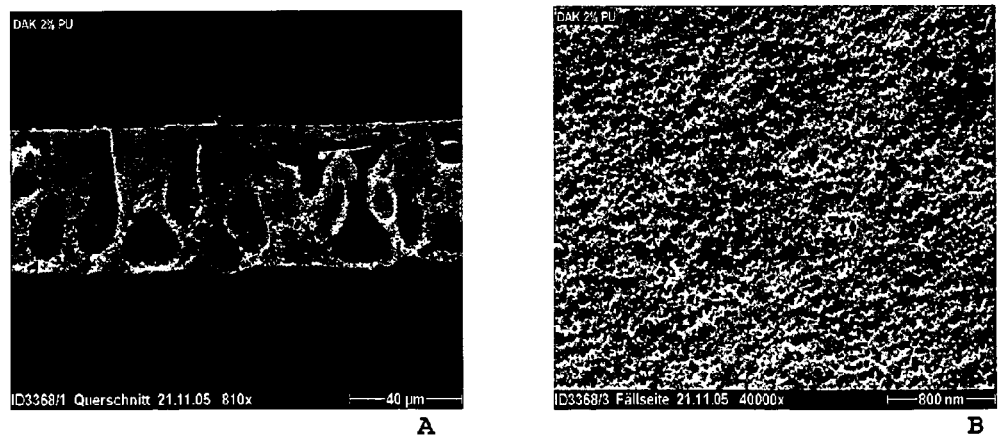

FIG. 8 shows the scanning electron micrograph of the cross-section (A) the flat sheet membrane prepared in Example 3. Magnification 810×. The white bar indicates 40 µm. Also shown is the surface of the membrane (B) (precipitated (non-glass) side). Magnification 40,000×. The white bar indicates 800 nm.

Figure 9:
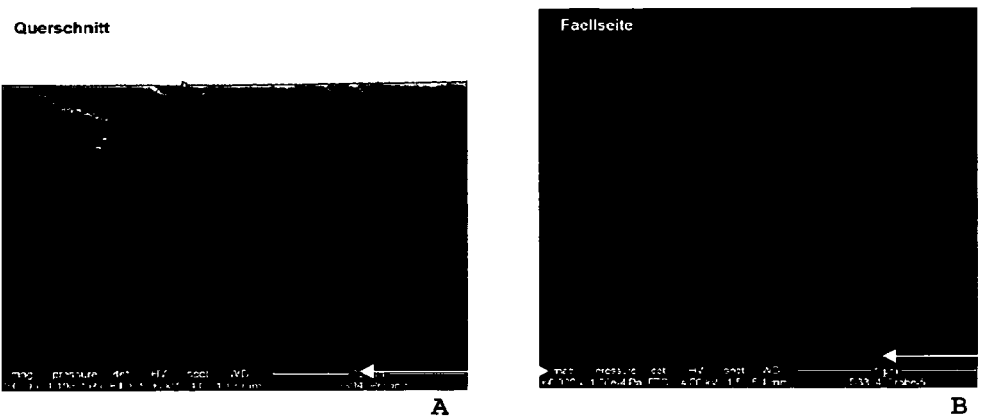

FIG. 9 shows the scanning electron micrograph of the cross-section (A) of the flat sheet membrane prepared in Example 4. Magnification 2,000×. The white bar indicates 30 µm. Also shown is the surface (B) of the membrane (precipitated (non glass) side). Magnification 60,000×. The white bar indicates 1 µm.

Figure 10:
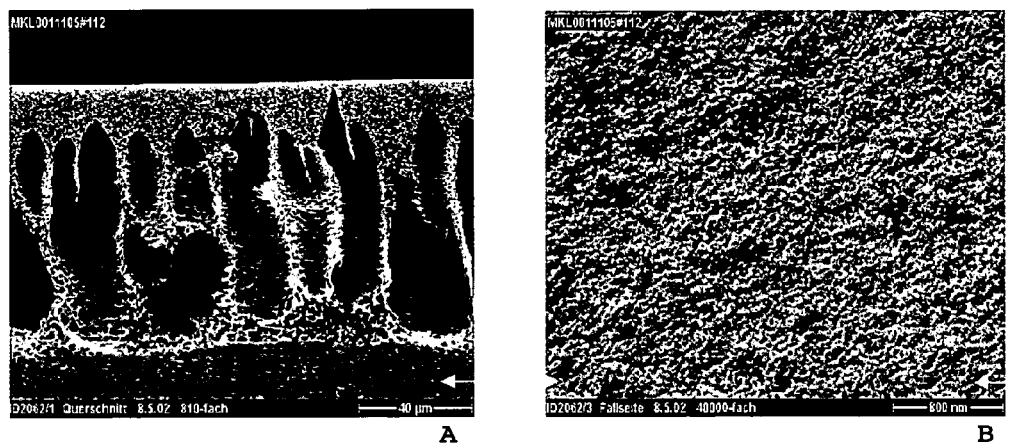

FIG. 10 shows the scanning electron micrograph of the cross-section (A) of the comparative flat sheet membrane prepared in Example 8, i.e. without any polyurethane. Magnification: 2,000×. The white bar indicates 30 µm. Also shown is the surface (B) of the membrane (precipitated (non glass) side). Magnification 60,000×. The white bar indicates 1 µm.

Figure 11:
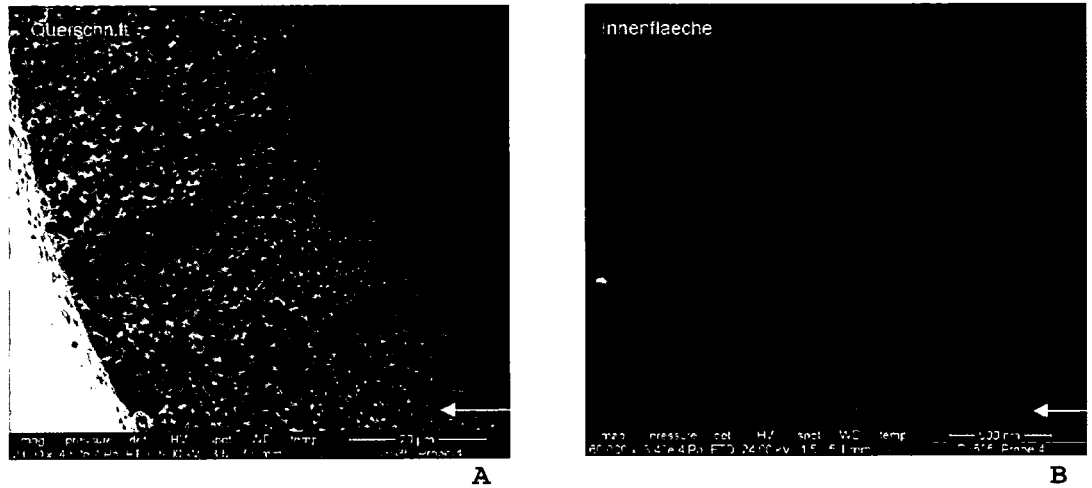

FIG. 11 shows the scanning electron micrograph of the cross-section (A) of the hollow fiber membrane prepared in Example 9. Magnification 2,000×. The white bar indicates 20 µm. Also shown is the inner surface (B). Magnification 60,000×. The white bar indicates 500 nm. The wall shows an asymmetric structure. The structure shows an overall sponge like structure. The inner surface is very smooth.

Figure 12:
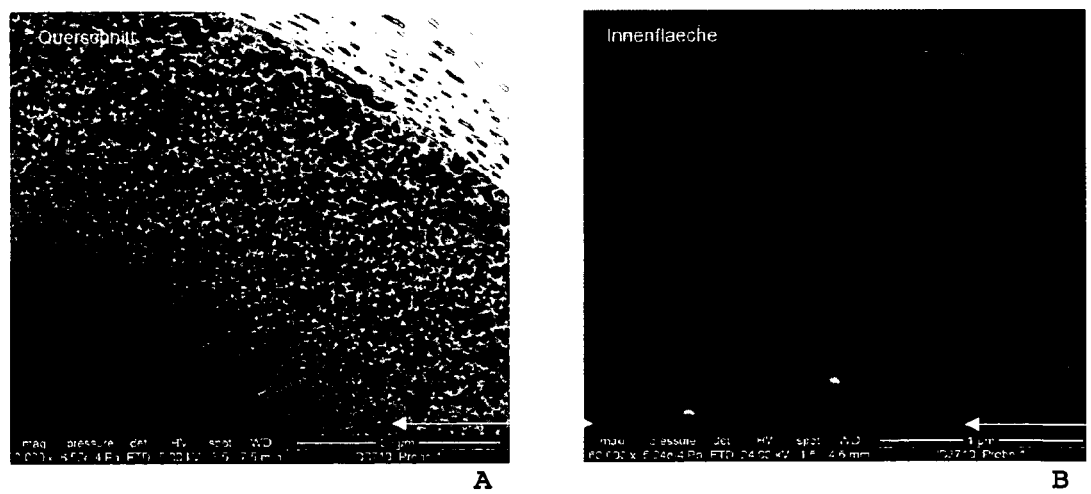

FIG. 12 shows the scanning electron micrograph of the cross-section (A) of the hollow fiber membrane prepared in Example 10. Magnification 2,000×. The white bar indicates 30 µm. Also shown is the inner surface (B) of the membrane. Magnification 60,000×. The white bar indicates 1 µm. The wall shows an asymmetric structure. The structure shows an overall sponge like structure. The inner surface is very smooth.

Figure 13:
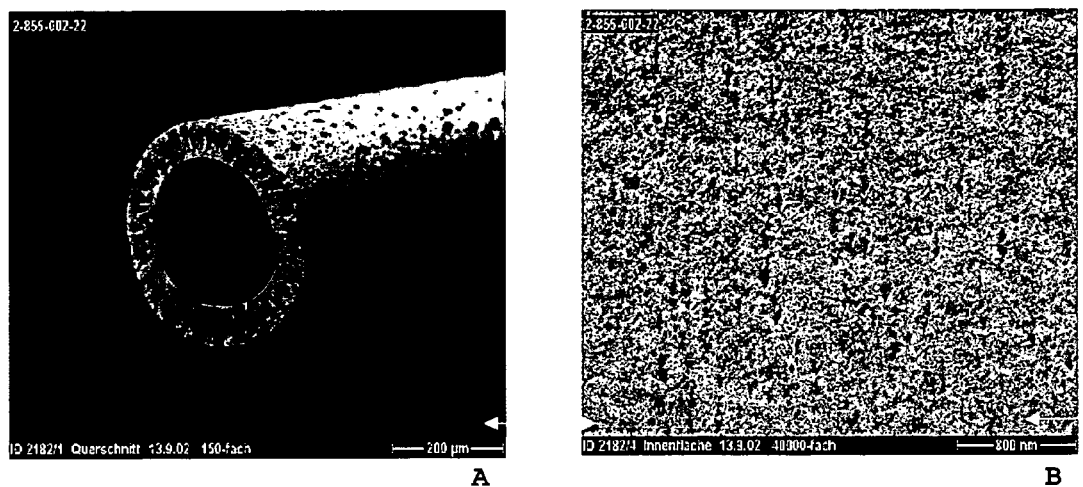

FIG. 13 shows the scanning electron micrograph of the cross-section (A) of the hollow fiber membrane prepared in Example 11. Magnification 2,000×. The white bar indicates 200 µm. Also shown is the inner surface (B) of the membrane. Magnification 40,000×. The white bar indicates 100 nm.

DETAILED DESCRIPTION OF THE INVENTION

In one aspect of the present invention, the membrane can be used for cell attachment or adherence and cell cultivation or expansion without the need to pre-treat or pre-coat the membrane with EMC. Advantages of using a membrane for cell cultivation without any such EMC are, for example, lower cost in terms of time savings and less process steps, a significantly reduced risk of contamination brought along with the EMC (GMP-compliance) or the higher number of process steps needed for coating a membrane and significantly better defined materials and protocols for cell production.

It is of course possible to additionally pre-treat or pre-coat the membrane of the present invention with one or more EMC which are generally known in the art. Especially for applications which are not intended for expanding or growing cells or tissues for re-implantation into the host, such pre-treatment may further improve the performance of the membrane in terms of adhesion or proliferation. However, it is always preferable to use the membrane without any coating with EMC.

In a further aspect of the present invention, the performance in expanding and culturing cells can be significantly improved by preparing a hollow fiber membrane according to the invention, and by using said hollow fiber membrane or a hollow fiber membrane bundle in a continuous culture process as an alternative to plate culture techniques.

In the context of the present invention, the expression "cell culture" or "culturing (of) cells" shall comprise the adherence, maintenance, growth, expansion, differentiation, molecular biological modification (e.g. transfection), and/or storage of cells of different types.

The membrane of the invention can be prepared in a way that confers the specific adhesive properties to the whole of the membrane, i.e., in case of a hollow fiber membrane for continuous applications, to the outside and inside of the hollow fiber membrane.

It is, however, also possible to prepare the membrane in a way that creates a cell adhesive surface on the outside or the inside (lumen side) of the hollow fiber membrane only. In case the cells are cultivated only on the inside of the hollow fibers, hollow fiber membranes according to the invention can be prepared which present their specific adhesive properties only on the inside of the hollow fibers. It is equally possible to prepare hollow fiber membranes according to the invention which have the specific adhesive properties only on the outside. Accordingly, the hollow fiber membranes of the invention can also be prepared and used in applications which require adhesion and cultivation of cells exclusively on the inside or the outside, respectively, in which case the polyurethane additive is present only in the inside or outside layer of the membrane, supported by a layer not containing any polyurethane. Such membranes can be prepared using a triple spinneret and two different polymer solutions.

In a further aspect of the present invention, the specific nature of the membrane also provides for a system for cellular co-cultivation of two or more different cell types.

A further aspect of the present invention is that the membrane very well promotes the formation of an optimal cell monolayer in terms of differentiation and integrity without having to pre-coat the membrane surface with any EMC. The membrane of the invention provides for the retention of typical cell morphology, a monolayer is readily formed and tight junctions can be created. In the context of the present invention, a monolayer refers to a layer of cells in which no cell is growing on top of another, but all are growing side by side and are in many cases touching each other on the same growth surface, even though this is not necessary for all potential applications of the membrane.

The membrane according to invention can thus be advantageously used, for example, (a) in tissue culture technology, i.e. for establishing bioartificial implants, such as bioartificial kidneys or livers (see also Atala (2006));

(b) for cultivating cells, i.e., adherent or suspended cells, in particular adherent cells, for use in medical therapies via injection of cells, which need to be expanded in vitro before being re-implanted into the host, such as, for example, MSC, smooth muscle cells, skin cells, nerve cells, neuroglia or endothelial cells in general;

(c) for expanding and providing cells which serve as producers of bio products such as growth factors, recombinant proteins, cytokines or antibodies, such as monoclonal antibodies;

(d) for preparing cultures of adherent cells, preferably cell monolayer cultures, for studying specific cell types or for studying the influence of any drugs on cells (screening procedures), such as, for example, anti-cancer agents, anti-fungals, antibiotics, anti-virals (including anti-HIV) and anti-parasitic drugs;

(e) or any other application which is based on or requires the culturing of cells, in particular adherent cells, in an in vitro system.

The membrane of the invention can have any suitable geometry according to the needs of the intended use, i.e. it can be used as a flat sheet, a hollow fiber or a bundle of hollow fibers, or can be shaped to form chambers or other geometries needed. The core unit for cell expansion preferably is a hollow fiber-based membrane system allowing sufficient exchange of $O_2$ and $CO_2$, supply of nutrients and removal of waste products. The surface of the membrane is designed to enable adhesion and proliferation of cells properties through specific surface characteristics. The advantages of the cultivation of cells inside hollow fibers is based on the advantageous surface to volume ratio which results in the minimization of medium consumption in the cultivation process, the minimization of space requirements and the minimization of labor, as compared to conventional flask or cell stack culture methods.

The membrane of the invention can be used in various kinds of cell expansion or cell culturing devices or systems, such as described, for example, in US 2003/0203478 A1, U.S. Pat. No. 6,150,164, or U.S. Pat. No. 6,942,879, all incorporated herein by reference.

The membrane of the present invention can advantageously be used for culturing adherent cells in general. Adherent cells are defined, in the context of the present invention, as cells attaching to a substrate which are to be maintained, expanded, differentiated, stored, etc. The membrane of the invention can be used for culturing, for example, stem cells, including embryonic and adult stem cells, especially mesenchymal stem cells (MSC); fibroblasts; epithelial cells; skin cells; nerve cells; hepatocytes; endothelial cells; muscle cells; chondrocytes, etc. In a particular embodiment of the invention, the membrane is used to cultivate mesenchymal stem cells (MSC).

The polymer solution used for preparing the membrane of the invention comprises from 11 to 19 wt.-% of a first polymer selected from the group consisting of polysulfone (PS), polyethersulfone (PES) and polyarylethersulfone (PAES), from 0.5 to 13 wt.-% of a second polymer such as polyvinylpyrrolidone (PVP), from 0.001 to 20 wt.-% of a polyurethane (PU), optionally from 0.01 to 2 wt.-% of a polyamide (PA), from 0 to 7 wt.-% of water, and, the balance to 100 wt.-%, of a solvent selected from the group consisting of N-methyl-2-pyrrolidone (NMP), N-ethyl-2-pyrrolidone (NEP), N-octyl-2-pyrrolildone (NOP), dimethyl acetamide (DMAC), dimethyl formamide (DMF), dimethyl sulfoxide (DMSO) and gamma-butyrolactone (GBL).

Said first polymer is preferably present in the polymer solution in an amount of from 13 to 14 wt.-%, especially preferably in an amount of from 13.6 to 14 wt.-%. Polyethersulfone (PES) and polyarylethersulfone (PAES) are preferably used for preparing the membrane of the invention.

Preferably, the polyvinylpyrrolidone (PVP) in the polymer solution consists of a blend of at least two homopolymers of polyvinylpyrrolidone with one of the homopolymers of polyvinylpyrrolidone (=low molecular weight PVP) having an average relative molecular weight of from about 10,000 g/mol to 100,000 g/mol, preferably about 30,000 g/mol to 70,000 g/mol, and another one of the homopolymers of polyvinylpyrrolidone (=high molecular weight PVP) having an average relative molecular weight of from about 500,000 g/mol to 2,000,000 g/mol, preferably about 800,000 g/mol to 2,000,000 g/mol. Examples of such PVP homopolymers are PVP K85, a high molecular weight PVP having a molecular weight of about 825,000 Da, and PVP K30, a low molecular weight PVP having a molecular weight of about 66,800 Da. In a preferred embodiment of the present invention the polymer solution for preparing the membrane comprises from 0.5 to 5 wt.-% of a high molecular weight PVP and from 1 to 8 wt.-% of a low molecular weight PVP.

In one embodiment of the present invention the polyurethane component is a thermoplastic polyurethane (TPU), preferably a polyurethane selected from the following group of polyurethanes: DESMOPAN® (Bayer MaterialScience AG), IROGRAN® (Huntsman), ISOPLAST® (The Dow Chemical Company), TECOTHANE® (Velox), CARBOTHANE® (Velox), TECOFLEX® (Velox), ESTANE® (Noveon). Among these polyurethanes, the following types are preferred: DESMOPAN® DP 9665DU, IROGRAN® D74 P 4778, ISOPLAST® 302 EZ, TECOTHANE® TT-1074A, CARBOTHANE® PC-3575A, TECOFLEX® EG-80 HI NCO and ESTANE® 58887 TPU. Polyurethanes which are especially useful for preparing membranes suitable for promoting cell adhesion and proliferation are DESMOPAN® and TECOTHANE® and their specific types mentioned before. The PU content in the polymer solution for preparing the membrane may vary from 0.001 wt.-% to 20 wt.-%. In a preferred embodiment of the present invention, the polymer solution contains from 0.1 wt.-% to 6 wt.-% of the polyurethane, more preferably from 0.5 wt.-% to 2 wt.-%. The PU content can be varied with regard to the cell type which is intended for cultivation.

The polymer solution optionally comprises from 0.01 to 2 wt.-%, preferably 0.01 to 0.5 wt.-%, more preferably 0.01 to 0.1 wt.-%, of a polyamide (PA). Preferred polyamides are amorphous polyamides based on trimethylhexamethylenediamine and terephthalic acid, e.g. polyamides available from Degussa/Evonik under the trade name Trogamid®, in particular those of the Trogamid® T series.

The water content of the spinning solution preferably is from 1 to 5 wt.-%, more preferably about 3 wt.-%.

Various solvents can be used for preparing a membrane according to the invention, such as N-methyl-2-pyrrolidone (NMP), N-ethyl-2-pyrrolidone (NEP), N-octyl-2-pyrrolildone (NOP), dimethyl acetamide (DMAC), dimethyl formamide (DMF), dimethyl sulfoxide (DMSO) or gamma-butyrolactone (GBL) and mixtures thereof. The solvent will be present in an amount representing the balance to 100 wt.-% of the polymer solution. Preferred solvents in the context of the present invention are N-methyl-2-pyrrolidone (NMP) and dimethyl acetamide (DMAC). N-methyl-2-pyrrolidone (NMP) is especially preferred. The content of the solvent in the polymer solution preferably is from 60 to 80 wt.-%, more preferably from 67 to 76.4 wt.-%.

In a specific embodiment of the present invention, the membrane is a hollow fiber membrane.

The hollow fiber membrane of the invention is characterized by generally having the narrowest pore size, i.e. the selective layer, on the inside of a hollow fiber. It is, however, possible to prepare a hollow fiber membrane with identical pore sizes on the inside and outside of the membrane. The preparation of such fibers is disclosed in WO 2008/046779, which is incorporated herein by reference. In general, it is preferable to have a smooth surface on the inside of a hollow fiber for promoting cell adhesion and proliferation on the lumen side of the hollow fiber membrane, especially for continuous applications.

The hollow fiber membrane of the invention is further characterized by having an inner diameter of from 50 to 2,000 μm, preferably of from 50 to 1,000 μm, and more preferably from 100 to 950 μm. The hollow fiber membrane has a wall thickness of from 10 to 200 μm, preferably of from 20 to 100 μm, and more preferably from 25 to 55 μm.

The thickness of a flat sheet membrane according to the invention may vary between 20 μm and 200 μm. A thickness of 35 μm to 50 μm may be especially advantageous for most applications.

The membrane according to the invention is a hydrophilic, semipermeable membrane. "Hydrophilic" membranes can be defined, in accordance with the present invention, by their ability to be spontaneously water-wettable without wetting aids. A membrane, independent of its shape, is called readily or spontaneously water-wettable if it is wetted by water virtually spotlessly. A semipermeable membrane allows nutrients and metabolizing gasses to pass from the cell-culture medium through the wall of the hollow fiber membrane to the cells, and cell waste products to pass from the cells to the medium on the other side of the membrane, while retaining the cells and, as the case may be, larger secreted products.

The hydraulic permeability (Lp) of a membrane of the invention may vary from about $0.1 \cdot 10^{-4}$ to $100 \cdot 10^{-4}$ cm$^3$/(cm$^2$ bar sec). In one embodiment of the present invention, the hydraulic permeability of the membrane is in the range of from $0.1 \cdot 10^{-4}$ to $10 \cdot 10^{-4}$ cm$^3$/(cm$^2$ bar sec), in particular from $0.1 \cdot 10^{-4}$ to $5 \cdot 10^{-4}$ cm$^3$/(cm$^2$ bar sec). For instance, the membranes of the invention can be so-called "low flux" membranes, having a molecular weight cut-off of about 20 kDa and a Lp of about $2 \cdot 10^{-4}$ to $5 \cdot 10^{-4}$ cm$^3$/(cm$^2$ bar sec).

In order to achieve such hydraulic permeabilities without getting defects in the membrane structure, the viscosity of the polymer solution should be in a range of from 2,500 centipoise (cP) to 200,000 cP, preferably from 10,900 cP to 25,600 cP for hollow fiber production. For flat sheet membrane production, the viscosity should be in a range of from 2,500 cP to 500,000 cP, preferably from 4,500 cP to 415,000 cP.

The membranes of the invention can be prepared, for example, in flat sheet or hollow fiber geometry. The membranes of the invention are further characterized by the smoothness or low roughness of the cell adhesion side.

Figure 1:
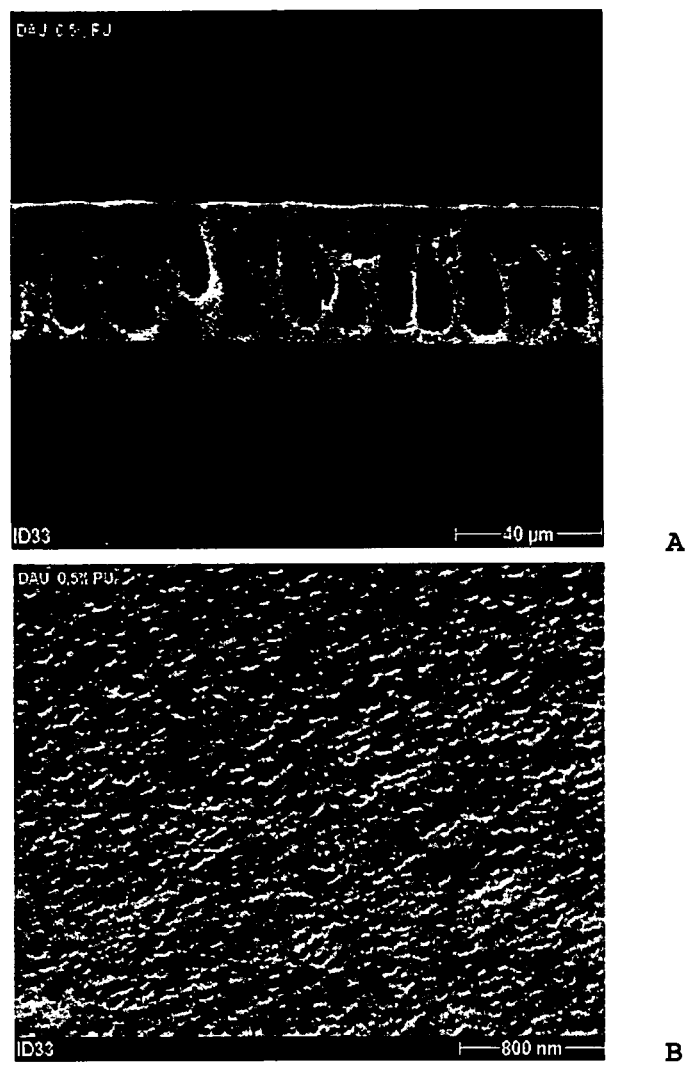
FIG. 1 (A) is a scanning electron micrograph of the cross-section of a flat sheet membrane (see Example 2) having a thickness of <50 μm with a magnification of 810×. The weight fractions of the different components in the polymer solution PS/PVP-K85/PVP-K30/PU/H2O/NMP are 14.0/3.0/5.0/0.5/3.0/74.5. The membrane has a 3-layer structure. The white bar indicates 40 μm.
Figure 2:
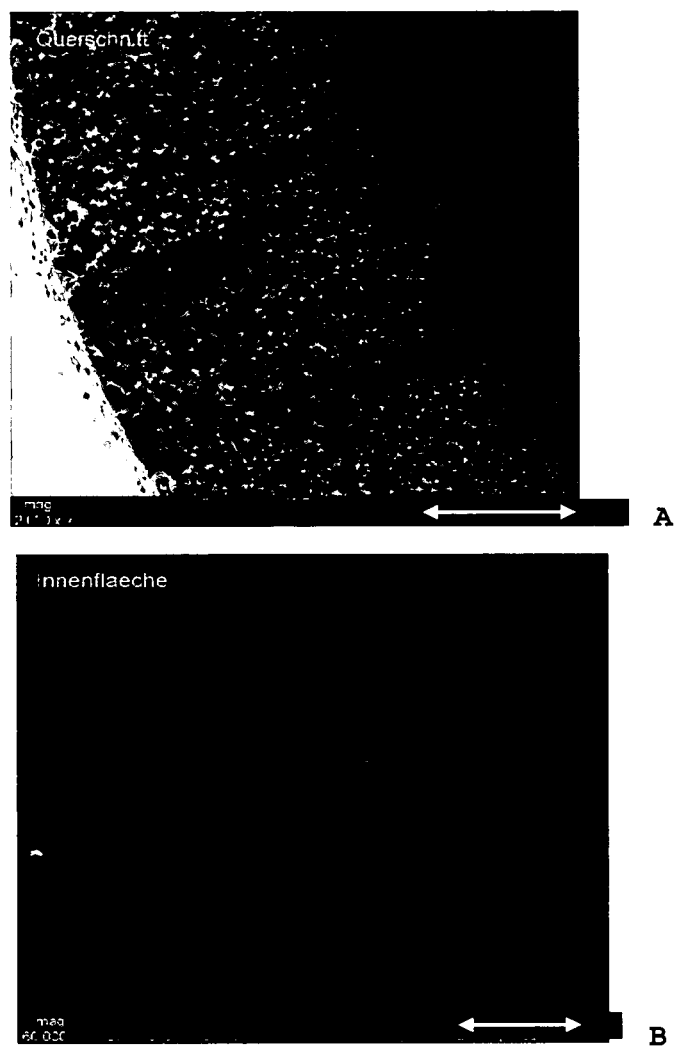
FIG. 2 (A) is a scanning electron micrograph (magnification: 2,000×) of the cross-section of a hollow fiber membrane having an inner diameter of 216 μm and an outer diameter of 318 μm. The weight fractions of the different components in the polymer solution PS/PVP-K85/PVP-K30/PU/H2O/NMP are 14.0/3.0/5.0/2.0/3.0/73.0. The wall structure is asymmetric and shows an overall sponge-like structure. The white arrow indicates 20 μm.

In one embodiment, the membrane of the invention has an asymmetric structure. In the case of hollow fibers, there is a thin separation layer on the inner side of the fibers. The structure or morphology of the membrane of the invention may otherwise vary without significant impact on its performance regarding cell adhesion and proliferation. The membrane may have, for example, a 3-layer structure or a sponge-like structure or a foam-like structure (FIGS. 1 and 2). In one embodiment of the invention, the membrane is a hollow fiber having an asymmetric, sponge-like structure.

The selective cut-off of a membrane for cell culture is essential for keeping essential substances in the lumen side by size exclusion. This is also of importance with regard to minimizing medium consumption in cases when growth medium is to be used only in the intracapillary (IC) side and not on the extracapillary side (EC) of hollow fiber membranes. In this case crucial components of fetal bovine serum (FBS) or platelet lysate-based media can be retained on the IC side and not diffuse from IC to EC and are no more available for cells located on the IC side. For the cultivation of MSC, the cut-off of the membrane of the present invention is in the range of from 1,000 to 60,000 Da, e.g. from 1,000 to 40,000 Da, or from 1,000 to 20,000 Da.

For preparing a flat sheet membrane according to the invention, the polymers are dissolved in the solvent at constant conditions. Degassing of the polymer solution is performed in a drying oven creating a vacuum (approximately 100 mbar). The temperature of the polymer solution may vary over a relatively broad range. It is advantageous to choose a temperature ranging from ambient temperature to up to 60° C.

It is advantageous for the preparation of flat sheet membranes to use a polymer solution comprising 13 to 14 wt.-% of PES, PS or PAES, 2 to 3 wt.-% of a high molecular weight PVP component, 4.5 to 6 wt.-% of a low molecular weight PVP component, 0.01 to 8 wt.-% of a polyurethane, 0 to 2 wt.-% of a polyamide, about 3 wt.-% $H_2O$, the balance to 100% of a solvent, advantageously an amount of from 67 to 76 wt.-%.

The final polymer solution is then cast as a uniform film onto a smooth surface such as a glass slide which acts as a supporting area, by utilizing a special coating knife. The velocity of casting the polymer film can vary over a relatively broad range. A velocity between 10 and 20 mm/s may be used. In an exemplary lab-scale process, the polymer solution first is applied steady-going onto the glass slide using a syringe. It is important to work bubble-free. The coating knife with a defined gap height is driven with constant velocity creating a uniform polymer film. For a good thickness distribution, a coating knife having a uniform gap is advisable.

The temperature of the polymer solution may vary. Temperatures from ambient temperature up to 60° C. can be advantageously used.

In one embodiment of the invention, the precipitation bath comprises $H_2O$ in an amount of from 30 to 100 wt. %, preferably in an amount of from 56 to 66 wt.-%, and a solvent, such as NMP, in an amount of from 0 to 70 wt.-%, preferably from 34 to 44 wt.-%. The temperature of the precipitation bath can be varied over a relatively broad range. It may be advantageous to apply a temperature between 0° C. and 80° C., or between 30° C. and 50° C. The precipitation time can also be varied. About five minutes generally is a suitable precipitation time. The precipitation bath preferably consists of $H_2O$ and a solvent. The bath preferably comprises $H_2O$ in amount of from 30 wt.-% to 100 wt.-% and a solvent selected from N-methyl-2-pyrrolidone (NMP), N-ethyl-2-pyrrolidone (NEP), N-octyl-2-pyrrolildone (NOP), dimethyl acetamide, dimethyl formamide (DMF), dimethyl sulfoxide (DMSO) or gamma-butyrolactone (GBL) and mixtures thereof in an amount of from 70 wt.-% to 0 wt.-%. In one embodiment of the invention, the precipitation bath comprises $H_2O$ in an amount of from 56 to 66 wt.-%, and a solvent in an amount of from 34 to 44 wt.-%. NMP is an especially suitable solvent in the context of the present invention.

The precipitated membrane is then stored in a non-solvent until the membrane is cut. After cutting, the membranes usually are washed, dried and sterilized. Examples for flat sheet membrane preparation are shown in Example 1 and Example 2 (see also FIG. 1).

The membrane of the invention can also be prepared in hollow fiber geometry. For preparing such a hollow fiber membrane, the solution is pumped through a spinning die and the liquid hollow fiber is formed. The NMP concentration in the center leads to an open structure at the inner side of the membrane. The smallest pores are directly at the inner side of the membrane. The overall structure (see FIGS. 2A and B) and the pores at the outside of the membrane are much bigger. The selective layer at the inside is in direct contact with cell medium.

It is advantageous for the preparation of hollow fiber membranes to use a polymer solution comprising 13 to 15 wt.-% of PES, PS or PAES, 2 to 4 wt.-% of a high molecular weight PVP component, 5 to 6 wt.-% of a low molecular weight PVP component, 0.5 to 2 wt.-% of a polyurethane, 0 to 0.5 wt.-% of a polyamide, 2 to 4 wt.-% $H_2O$, filled up to 100% with a solvent, such as NMP, advantageously in an amount of from 73 to 75 wt.-%. The viscosity of the polymer solution is in the range of from 2,500 to 200,000 cP. In a specific embodiment of the present invention, the viscosity is in the range of from 10,900 to 25,600 cP.

The bore liquid solution comprises $H_2O$ in an amount of from 30 to 100 wt.-%, advantageously from 56 to 80 wt.-% and a solvent such as NMP in an amount of from 0 to 70 wt.-%, advantageously from 20 to 44 wt.-%.

In one embodiment, the precipitation bath consists of water. The temperature of the precipitation bath can be varied over a broad range, but ambient temperature up to about 40° C. can advantageously be used in the process. The distance between the die and the precipitation bath generally is in the range of from 50 to 100 cm. The die (spinneret) temperature can also be varied. Temperatures between 20 and 80° C. can be used. It may be advantageous to apply temperatures between 40 and 55° C. The spinning speed may be chosen to be from 11 to 40 m/min.

In one embodiment of the invention, the resulting Lp for a hollow fiber membrane of the invention is in the range of from $0.1 \cdot 10^{-4}$ to $100 \cdot 10^{-4}$ $cm^3/(cm^2 \cdot bar \cdot s)$, $0.1 \cdot 10^{-4}$ to $10 \cdot 10^{-4}$ $cm^3/(cm^2 \cdot bar \cdot s)$, more preferably $0.1 \cdot 10^{-4}$ to $5 \cdot 10^{-4}$ $cm^3/(cm^2 \cdot bar \cdot s)$.

There are two ways for producing membranes according to the invention which may be referred to a "wet" and "dry". In case "wet" fibers are prepared, the membranes have to be dried separately in a tube or an oven after they have been prepared. To this end, bundles of fibers (for example from 30 to 15,000 fibers) are placed in a plastic or metal tube. Hot air is passed through this tube within the bundles to dry the fibers.

The second way is "online-drying" which is an efficient way to directly prepare dry fibers on a spinning machine. Both procedures are applicable to arrive at membranes according to the invention.

A further aspect of the invention is a cell culturing device comprising a membrane of the invention. Examples of cell expansion or cell culturing devices or systems which can be modified to comprise the membrane of the invention are disclosed in US 2003/0203478 A1, U.S. Pat. No. 6,150,164, or U.S. Pat. No. 6,942,879, all incorporated herein by reference. The device can comprise a stack of flat sheet membranes of the invention or a bundle of hollow fiber membranes of the invention.

In one embodiment of the device, the membrane forms an interface between two fluid compartments of the device. The device can be similar in construction to commercially available filtration devices used, for example, in hemodialysis or hemofiltration.

An exemplary device comprises two compartments separated by a semipermeable membrane mounted in a casing, a first internal compartment fitted with two accesses and a second external compartment comprising one or two accesses, both compartments being also separated by a potting compound, based on an appropriate adhesive compound, intended for forming as applicable (i) a cylindrical partition separating both compartments of said device containing a semipermeable membrane of the hollow fiber bundle type as defined above or (ii) a tight seal in said device including a semipermeable membrane of the sheet membrane type as defined above.

Another exemplary device comprises a plurality of hollow fiber membranes, contained within an outer shell, and configured so that fluid within a space external to the hollow fibers (i.e., an extracapillary compartment) is segregated from fluid passing through the hollow fibers and their corresponding orifices. Additionally, the device includes two manifold end chambers within the outer shell on opposite ends of the device. Each of the two orifices of a hollow fiber connects to a different end chamber. The end chambers and the extracapillary compartment are separated by the semipermeable membranes of the hollow fibers. The composition within the extracapillary compartment can be controlled, to a certain extent, by the molecular weight cutoff, or pore size, of the membranes of the hollow fibers.

In one mode of operating the device, cells are grown in the extracapillary compartment while a nutrient medium is passed through the hollow fibers. In another mode of operating the device, cells are grown in the intracapillary space (i.e. lumen) of the hollow fibers while a nutrient medium is passed through the extracapillary compartment and/or the intracapillary compartment. The semipermeable nature of the hollow fibers allows nutrients and cell waste products to pass through the walls of the hollow fibers while blocking cells from doing the same.

Shell-and-tube type bioreactors provide several advantages. For adherent cells, the use of several hollow fibers provides, within a relatively small volume, a large amount of surface area upon which the cells can grow. This large amount of surface area also facilitates localized distribution of nutrient media to the growing cells and ready collection of cell waste products. Shell-and-tube type bioreactors enable the growth of cells at much higher density rates than is possible with other cell culture devices. They can support cell densities greater than $10^8$ cells per milliliter, whereas other cell culture devices are typically limited to densities around $10^6$ cells per milliliter.

A further aspect of the invention provides a device for the extracorporeal treatment of body fluids, comprising cells and a membrane of the invention. In one embodiment, the cells are adherent cells which form a confluent layer on a surface of the membrane, for instance the surface of the lumen of a hollow fiber membrane of the invention, or the outer surface of a hollow fiber membrane of the invention. For the rest, the design of the device can be similar to the design described above for the cell culturing device. The body fluid to be treated is conducted through a fluid space of the device where it passes over the cell layer, allowing the cells to extract components from the body fluid, to metabolize components of the body fluid, or to segregate components into the body fluid.

EXAMPLES

Preparation of Hand Bundles

The preparation of the membrane bundle after the spinning process is necessary to prepare the fiber bundle for the following performance tests. The first process step is to cut the fiber bundles to a defined length of 23 cm. The next process step consists of melting the ends of the fibers. An optical control ensures that all fibers are well melted. Then, the ends of the fiber bundle are transferred into a potting cap. The potting cap is fixed mechanically and a potting tube is put over the potting caps. Then the fibers are potted with polyurethane. After the polyurethane has hardened, the potted membrane bundle is cut to a defined length and stored dry before it is used for the different performance tests.

Preparation of Mini-Modules

Mini-modules [=fiber bundles in a housing] are prepared in a similar manner. The mini-modules ensure protection of the fibers and are used for steam-sterilization. The manufacturing of the mini-modules differs in the following points:

The number of fibers required is calculated for an effective surface A of 360 cm² according equation (1)

$$A = \pi \times d_i \times 1 \times n \, [cm^2] \tag{1}$$

with
$d_i$=inner diameter of fiber [cm]
n=amount of fibers
l=effective fiber length [cm]

The fiber bundle is cut to a defined length of 20 cm
The fiber bundle is transferred into the housing before the melting process
The mini-module is put into a vacuum drying oven over night before the potting process Preparation of Filters The filter (=dialyzer) comprises about 8,000-10,000 fibers with an effective surface area of 1.4 m². A filter is characterized by a cylindrical housing with two connectors for the dialyzing fluid and caps applied on both ends, each with one centered blood connector. The manufacturing process (after winding) can be divided into the following main steps:

the cut bundles (length approx. 30 cm) are transferred into the housing with a special bundle claw;
both ends of the bundles are closed by a closing process
the fibers are potted into the housing with polyurethane (PUR);
the ends are cut to open the fibers;
the caps are welded to the blood connectors using ultrasonic welding;
final treatment comprises: rinsing, integrity testing, final drying
the filters are packed in sterile bags and steam sterilized.

Preparation of Flat Sheet Inserts

Flat membranes are immobilized on glass plates. Polyurethane functioning as glue for inserts is evenly distributed on a plate. The inserts are gently immersed in polyurethane and immediately glued onto the respective membrane. Inserts are weighed down with a glass and iron plate and dried for 16 to 18 hours. Flat membrane inserts are cut out and welded into sterilization bags. Finally, inserts may be sterilized in an autoclave at 121° C.

Hydraulic Permeability (Lp) of Hand Bundles and Mini-Modules

The hydraulic permeability of a membrane bundle is determined by pressing a defined volume of water under pressure through the membrane bundle, which has been sealed on one side, and measuring the required time. The hydraulic permeability can be calculated from the determined time, the effective membrane surface area, the applied pressure and the volume of water pressed through the membrane. From the number of fibers, the fiber length as well as the inner diameter of the fiber, the effective membrane surface area is calculated. The membrane bundle has to be wetted thirty minutes before the Lp-test is performed. For this purpose, the membrane bundle is put in a box containing 500 ml of ultapure water. After 30 minutes, the membrane bundle is transferred into the testing system. The testing system consists of a water bath that is tempered at 37° C. and a device where the membrane bundle can be implemented mechanically. The filling height of the water bath has to ensure that the membrane bundle is located underneath the water surface in the designated device. To avoid that a leakage of the membrane leads to a wrong test result, an integrity test of the membrane bundle and the test system has to be carried out in advance. The integrity test is performed by pressing air through the membrane bundle that is closed on one side of the bundle. Air bubbles indicate a leakage of the membrane bundle or the test device. It has to be checked if the leakage can be associated with the wrong implementation of the membrane bundle in the test device or if a real membrane leakage is present. The membrane bundle has to be discarded if a leakage of the membrane is detected. The applied pressure of the integrity test has to be at least the same value as the applied pressure during the determination of the hydraulic permeability in order to ensure, that no leakage can occur during the measurement of the hydraulic permeability because of a too high-applied pressure.

Diffusive Permeability of Hand Bundles

Diffusion experiments with isotonic chloride solution as well as phosphate diluted in dialysis fluid (100 mg/L) are carried out to determine the diffusion properties of a membrane. A hand bundle is put in a measuring cell. The measuring cell allows passing the particular solution at the inside of the hollow fiber. Additionally, the measuring cell is filled completely with water and a high cross flow of distilled water is set to carry away the particular ions that pass the membrane cross section from the inside of the hollow fiber to the outside. By adjusting the pressure ratios correctly, a zero filtration is aimed for, so that only the diffusion properties of the membrane are determined (by achieving the maximum concentration gradient of the particular ion between the inside of the hollow fiber and the surrounding of the hollow fiber) and not a combination of diffusive and convective properties. A sample from the pool is taken at the beginning and a sample of the retentate is taken after 10 and 20 minutes. The chloride samples are then titrated with silver nitrate solution to determine the chloride concentration. The phosphate samples are analyzed photometrically. From the concentrations determined, the effective membrane surface area A and the flow conditions, the permeability P, of chloride or phosphate, respectively, can be calculated according to the following equation (2):

$$P_x [10^{-4} cm/s] = [Q_B/60/A] * \ln[(c_A - c_D)/c_R] * 10^4 \tag{2}$$

with
P=diffusive permeability [cm/s]
c=concentration [mmol]
A=effective membrane surface [cm²]
indices:
x=substance (here: chloride or phosphate, respectively)
A=starting concentration (feed)
D=dialysate
R=retentate
$Q_B$=blood flow [ml/min]

Sieving Coefficient for Myoglobin in Aqueous Solution (Hand Bundle)

The Sieving Coefficient of myoglobin is determined in aqueous solution. The concentration of myoglobin dissolved in PBS buffer is 100 mg/L. The expiry date of the aqueous solution is between 4 and 8 weeks. The solution has to be stored in the refrigerator. Prior to the Sieving Coefficient experiment, a Lp-test is performed using the method described earlier. The myoglobin sieving coefficient experiment is run in single pass whereas testing conditions are defined as follows:

The intrinsic flow rate ($J_v$ in cm/s) and wall shear rate ($\gamma$ in $s^{-1}$) are fix whereas the blood flow ($Q_B$) and filtration rate (UF) is calculated (see equation (4)+(5)):

$$Q_B[\text{ml/min}] = \gamma \cdot n \cdot \pi \cdot d_i^3 \cdot 60/32 \quad (4)$$

$$UF[\text{ml/min}] = J_V \cdot A \cdot 60 \quad (5)$$

with
n=amount of fibers
$d_i$=inner diamete of fiber [cm]
$\gamma$=shear rate [$s^{-1}$]
A=effective membrane surface [$cm^2$]

whereas A is calculated according to equation (1).

Testing a hand bundle or a mini-module the shear rate is set to 500 $s^{-1}$ and the intrinsic flow rate is defined to be $0.38 \cdot 10^{-04}$ cm/s.

The first samples are taken after 15 minutes (pool, retentate, and filtrate) and a second time after 60 min. At the end, the test-bundle is rinsed for some minutes with PBS-buffer then the test is stopped.

Contact Angles at the Solid-Water Interface: Polar-Dispersive Ratio

Contact angles and the ratio of polar and dispersive components of surface energy were determined using the captive bubble method developed by Andrade et al. (J. Polymer Sci: Polymer Symp. 66 (1979) 313-336).

Cell Adhesion and Proliferation Experiments

Cryo-preserved and culture-expanded bone marrow-derived multipotent mesenchymal stromal cells (MSC) and, for some cases, MSC in unprocessed bone marrow were used for adhesion and proliferation experiments. Tissue culture polystyrene (TCPS) plates and/or polyethylene terephthalate (PET) inserts were used as control materials. Cryo-preserved MSC were thawed, seeded, and expanded in conventional PS flasks. At various passages ranging from 2 to 7, MSC were seeded at 5,000 MSCs/$cm^2$ on materials and allowed to attach for 24 hours. Thereafter, MSCs were detached from materials by means of trypsinization. Cell number was assessed by CASY counting. The number of attached MSC were compared to TCPS and/or PET plates or inserts and expressed as percentage.

For cell proliferation experiments, MSC were seeded at 500 or 5,000 MSCs/$cm^2$ and allowed to grow to pre-confluency. Subsequently, MSC were detached from materials by means of trypsinization. Cell number was assessed by CASY counting. The number of expanded MSC was compared to TCPS and/or PET and expressed as percentage. Selected membranes were used for long-term culture. MSC were passaged several times and membranes were used up to 8 weeks. After each trypsinization, MSC were seeded on the same membranes at 500 MSCs/$cm^2$. For MSC characterization, immunophenotype of MSC, differentiation potential exemplarily shown for the adipogenic (FIG. 5) lineage, and morphology after plastic adherence were assessed.

In the cell adhesion and proliferation experiments, cells (MSC) from different donors were used. It is known that there are donor-related variations in MSC behavior. For this reason, MSC adhesion and proliferation data are related to standard cell culture media such as tissue culture polystyrene (TCPS) and porous (pore size 1 μm) polyethylene terephthalate (PET) inserts (see also Table I).

Adipose Differentiation of MSC After Culture on Synthetic, Polyurethane-Containing Membranes It is important that cells which are cultured/expanded in an in vitro system and on synthetic matrices retain their basic abilities. For example, stem cells, such as mesenchymal stem cells (MSC) should retain their ability to differentiate after adhesion to and expansion on such membrane. The ability of MSC to differentiate into adipocytes after expansion on flat sheet membranes prepared according to the invention with different amounts of polyurethane in the polymer solution (see Examples 1 and 2), i.e. 0.5 wt.-% and 2 wt.-%, was tested (FIG. 5). In parallel, MSC were cultivated on standard TCPS. MSC were cultured in alpha-MEM medium, supplemented with 10% FCS, 1% penicillin/streptomycin and 1% ultra-glutamine. The medium for adipose induction contained the culture medium, supplemented with 50 μg/ml vitamin C, 1 μM dexamethasone, 10 μg/ml insulin, 0.5 mM IBMX (3-isobutyl-1-methyl-xanthine) and 50 μM indomethacine. The first induction was performed three days after confluence, followed by medium exchange and induction every two to three days. The fixation of the cells was done after 14 days. The differentiation of MSC cultivated on polyurethane-containing membranes was as good as on standard TCPS.

Example 1

Preparation of a Flat Sheet Membrane

A polymer solution was prepared by dissolving polyethersulfone (Ultrason® 6020, BASF)), polyvinylpyrrolidone (K30 and K85, BASF), polyurethane (Desmopan® 9665 DU, Bayer MaterialScience AG) as well as distilled water in N-methylpyrrolidone (NMP). The weight fraction of the different components in the polymer spinning solution, PES/PVP(K85)/PVP(K30)/9665DU/$H_2O$/NMP was 14/3/5/2/3/73. The viscosity of the resulting polymer solution was 21,000 mPa·s.

The polymers PES, PVP as well as polyurethane were dissolved in NMP and water at 60° C. until a clear, highly viscous solution was obtained. The solution was filtrated and degassed. Degassing of the polymer solution was performed in a drying oven at increased temperature (<100° C.) and reduced pressure (approximately 100 mbar).

The final polymer solution was then cast (automatically) as uniform film onto a smooth surface (glass slide) which acted as supporting area by utilizing a special coating knife. First, the polymer solution was heated to 60° C. in an oven and then directly applied steady-going onto the glass slide using a syringe. The coating knife with a defined height of gap (100 μm) was driven with a constant velocity of 12.5 mm/s, thus creating a uniform polymer film. This glass slide with the thin polymer film was quickly dipped into the coagulation bath. As coagulation bath, a water/NMP mixture containing 56 wt.-% water and 44 wt.-% NMP was used at 50° C. The precipitation of the membrane took about 5 minutes. Subsequently, the precipitated membrane was taken out, stored in non-solvent until all membranes of a series were prepared and then cut into a defined size. After cutting, the membranes were washed with distilled water for 30 minutes at 70° C., dried in an oven at 60° C. over night and finally packed in special bags used for sterilization. The membrane thickness was 35 μm.

The results achieved with this membrane in cell culture and the polar-dispersive ratio are shown in Table I.

TABLE I

MSC adhesion and proliferation on various polyurethane (PU) based flat sheet membranes as compared with standard tissue culture polystyrene (TCPS) and polyethylene terephthalate (PET) membranes. The polar-dispersive ratio of the respective membranes is also shown.

| Ex. | PU Content [wt.-%] | PU Type | MSC Adhesion Rel. to TCPS (%) | MSC Adhesion Rel. to PET (%) | MSC Proliferation Rel. to TCPS (%) | MSC Proliferation Rel. to PET (%) | Polar Dispersive Ratio |
|---|---|---|---|---|---|---|---|
| 1 | 2 | 9665 DU | n.d. | 90.2 | 115.6 | 96.8 | 1.75 |
| 2 | 0.5 | 9665 DU | n.d. | 88.1 | 116.3 | 97.4 | 1.67 |
| 3 | 4 | 9665 DU | n.d. | 89.5 | 146.2 | 136.1 | 1.89 |
| 4 | 0.5 | Irogran ® D74 P 4778 | 80.9 | 143.0 | 57.3 | 55.0 | 1.38 |
| 5 | 4 | Tecothane ® TT-1074A | 81.9 | 103.9 | 99.6 | 92.7 | 0.90 |
| 6 | 4 | Carbothane ® PC-3575 A | 83.7 | 106.1 | 76.0 | 73.5 | 1.16 |
| 7 | 4 | Estane ® 58887 NAT 038 P | 81.1 | 102.9 | 81.1 | 75.5 | 0.95 |
| 8 | 0 | no PU | n.d. | 14.3 | n.d. | 19.6 | 0.58 |

Example 2

Preparation of a Flat Sheet Membrane

A polymer solution was prepared by dissolving polyethersulfone (Ultrason® 6020, BASF), polyvinylpyrrolidone (K30 and K85, BASF), polyurethane (Desmopan® 9665 DU, Bayer MaterialScience AG) as well as distilled water in N-methylpyrrolidone (NMP). The weight fraction of the different components in the polymer spinning solution, PES/PVP(K85)/PVP(K30)/9665DU/$H_2O$/NMP was 14/3/5/0.5/3/74.5. The viscosity of the polymer solution was 10,300 mPa·s.

The polymer preparation procedure and the membrane formation procedure was as described in Example 1. The velocity of polymer casting was 20 mm/s. The membrane thickness was 35 μm. A scanning electron micrograph of the cross-section and the surface of the membrane (precipitated side) are shown in FIG. 1. The results achieved with this membrane in cell culture and the polar-dispersive ratio are shown in Table I.

Example 3

Preparation of a Flat Sheet Membrane

A polymer solution was prepared by dissolving polyethersulfone (Ultrason® 6020, BASF), polyvinylpyrrolidone (K30 and K85, BASF), the polyurethane (Desmoparn® 9665 DU, Bayer MaterialScience AG) as well as distilled water in N-methylpyrrolidone (NMP). The weight fraction of the different components in the polymer spinning solution, PES/PVP(K85)/PVP(K30)/9665DU/$H_2O$/NMP was 14/3/5/4/3/71. The viscosity of the polymer solution was 57,410 mPa·s.

The polymer preparation procedure as well as the membrane formation procedure and the remaining process steps were kept as described in Example 1.

The membrane thickness was ≦50 μm. A scanning electron micrograph of the cross-section and the surface of the membrane (precipitated side) are shown in FIG. 8. The results achieved with this membrane in cell culture and the polar-dispersive ratio are shown in Table I.

Example 4

Preparation of a Flat Sheet Membrane

A polymer solution was prepared by dissolving polyethersulfone (Ultrason® 6020, BASF), polyvinylpyrrolidone (K30 and K85, BASF), polyurethane (Irogran® D 74 P 4778, Huntsman) as well as distilled water in N-Methylpyrrolidone (NMP). The weight fraction of the different components in the polymer spinning solution, PES/PVP(K85)/PVP(K30)/Irogran/$H_2O$/NMP was 14/3/5/0.5/3/74.5. The viscosity of the polymer solution was 10,710 mPa·s.

The polymer preparation procedure, the membrane formation procedure and the remaining process steps were changed in comparison to description of Example 1 in the following points:

Temperature polymer preparation: 80° C.
Water/NMP wt.-% in coagulation bath: 66/34 wt.-%
Temperature of coagulation bath: 30° C.
Temperature of polymer solution during casting: Ambient temperature.

The membrane thickness was ≦50 μm. A scanning electron micrograph of the cross-section and the surface of the membrane (precipitated side) are shown in FIG. 9. The results achieved with this membrane in cell culture and the polar-dispersive ratio are shown in Table I.

Example 5

Preparation of a Flat Sheet Membrane

A polymer solution was prepared by dissolving polyethersulfone (Ultrason® 6020, BASF), polyvinylpyrrolidone (K30 and K85, BASF), polyurethane (Tecothane® TT-1047A, Velox) as well as distilled water in N-Methylpyrrolidone (NMP). The weight fraction of the different components in the polymer spinning solution, PES/PVP (K85)/PVP (K30)/Tecothane/$H_2O$/NMP was 14/3/5/4/3/71. The viscosity of the polymer solution was 46,820 mPa·s.

The polymer preparation procedure was as shown in Example 1, except for the following points:
Water/NMP wt.-% in coagulation bath: 66/34 wt.-%
Temperature of coagulation bath: 30° C.
Temperature of polymer solution during casting: Ambient temperature.

The membrane thickness was <50 μm. The results achieved with this membrane in cell culture and the polar-dispersive ratio are shown in Table I.

Example 6

Preparation of a Flat Sheet Membrane

A polymer solution was prepared by dissolving polyethersulfone (Ultrason® 6020, BASF), polyvinylpyrrolidone (K30 and K85, BASF), polyurethane (Carbothane® PC-3575 A, Velox) as well as distilled water in N-methylpyrrolidone (NMP). The weight fraction of the different components in the polymer spinning solution, PES/PVP (K85)/PVP (K30)/Carbothane/$H_2O$/NMP was 14/3/5/4/3/71. The viscosity of the polymer solution was 40,050 mPa·s.

The polymer preparation procedure was as shown in Example 1, except for the following points:
Water/NMP wt.-% in coagulation bath: 66/34 wt.-%
Temperature of coagulation bath: 30° C.
Temperature of polymer solution during casting: Ambient temperature.

The membrane thickness was <50 μm. The results achieved with this membrane in cell culture and the polar-dispersive ratio are shown in Table I.

Example 7

Preparation of a Flat Sheet Membrane

A polymer solution was prepared by dissolving polyethersulfone (Ultrason® 6020, BASF), polyvinylpyrrolidone (K30 and K85, BASF), polyurethane (Estane® 58887 NAT 038 P, Velox) as well as distilled water in N-methylpyrrolidone (NMP). The weight fraction of the different components in the polymer spinning solution, PES/PVP(K85)/PVP(K30)/Estane/$H_2O$/NMP was 14/3/5/4/3/71. The viscosity of the polymer solution was 51,000 mPa·s.

The polymer preparation procedure was as described in Example 1, except for the following points:
 Water/NMP wt.-% in coagulation bath: 66/34 wt.-%
 Temperature of coagulation bath: 30° C.
 Temperature of polymer solution during casting: Ambient temp.

The membrane thickness was <50 μm. The results achieved with this membrane in cell culture and the polar-dispersive ratio are shown in Table I.

Example 8

Preparation of a Comparative Flat Sheet Membrane Without Polyurethane

A polymer solution was prepared by dissolving polyethersulfone (Ultrason® 6020, BASF), polyvinylpyrrolidone (K30 and K85, BASF), as well as distilled water in N-methylpyrrolidone (NMP). The weight fraction of the different components in the polymer spinning solution, PES/PVP(K85)/PVP(K30)/$H_2O$/NMP was: 13.6/2/5/3/76.4. The viscosity of the polymer solution was 4,518 mPa·s.

The polymer preparation procedure as well as the membrane formation procedure and the remaining process were as described in Example 1.

The membrane thickness was 45 μm. A scanning electron micrograph of the cross-section and the surface of the membrane (precipitated side) are shown in FIG. 10. The results achieved with this membrane in cell culture and the polar-dispersive ratio are shown in Table I.

Example 9

Preparation of a Hollow Fiber Membrane

A polymer solution was prepared by dissolving polyethersulfone (Ultrason® 6020, BASF), polyvinylpyrrolidone (K30 and K85, BASF), the polyurethane (Desmopan® PU 9665 DU, Bayer MaterialScience AG) as well as distilled water in N-methylpyrrolidone (NMP). The weight fraction of the different components in the polymer spinning solution, PES/PVP(K85)/PVP(K30)/9665 DU/$H_2O$/NMP was 14/3/5/2/3/73. The viscosity of the polymer solution was 22,900 mPa·s.

The polymers PES, PVP as well as polyurethane were dissolved in NMP and water at 50 C until a clear and highly viscous solution was obtained. The warm solution was cooled to 20° C. and degassed.

A membrane was formed by heating the polymer solution to 50° C. and passing the solution through a spinning die. As bore liquid a water/NMP mixture containing 56 wt.-% water and 44 wt.-% NMP was used. The temperature of the die was 50° C. The hollow fiber membrane was formed at a spinning speed of 40 m/min. The liquid capillary leaving the die was passed into a water bath having ambient temperature. The length of the distance between the die and the precipitation bath was 100 cm. The formed hollow fiber membrane was guided through water baths. The wet hollow fiber membrane was then dried and had an inner diameter of 216 μm and an outer diameter of 318 μm. The membrane had a fully asymmetric membrane structure. The active separation layer of the membrane was at the inner side. The active separation layer was defined as the layer with the smallest pores. The structure shows an overall sponge like structure. The inner surface shows very smooth pores. The membranes were wound on a winding wheel and hand bundles with 200 fibers were prepared according to the method described below. A scanning electron micrograph of the cross-section and the inner surface of the membrane are shown in FIG. 11. The hydraulic permeability (Lp value) of the membrane was measured on hand bundles. The membrane showed a hydraulic permeability of $3.7 \cdot 10^{-4}$ $cm^3/(cm^2$ bar sec). Additionally, the sieving coefficient of myoglobin was measured. A sieving coefficient of 1.5% was obtained after 15 minutes and a sieving coefficient of 1.1% was obtained after 60 minutes. Subsequently, the hydraulic permeability (Lp value) of the membrane was measured again and was $2.7 \cdot 10^{-4}$ $cm^3/(cm^2$ bar sec). Furthermore, experiments regarding the diffusive permeability of the membrane were performed with chloride, inulin and vitamin $B_{12}$. The permeabilities for chloride, inulin and vitamin $B_{12}$ were $10.5 \cdot 10^{-4}$ cm/sec, $3.7 \cdot 10^{-4}$ cm/sec and $4.0 \cdot 10^{-4}$ cm/sec, respectively.

In addition, filters with an effective surface area of 0.9 $m^2$ were produced, packed in special plastic bags and finally gamma-sterilized (dose 25 kGy). Hand bundles (200 fibers) from such filter were prepared and the following measurements were carried out. The hydraulic permeability (Lp value) of the membrane was measured and showed a value of $2.4 \cdot 10^{-4}$ $cm^3/(cm^2$ bar sec). Additionally, the sieving coefficient of myoglobin was measured. A sieving coefficient of 2.2% was obtained after 15 minutes and a sieving coefficient of 2.9% was obtained after 60 minutes. Subsequently, the hydraulic permeability (Lp value) of the membrane was measured again and was $2.4 \cdot 10^{-4}$ $cm^3/(cm^2$ bar sec). Furthermore, experiments regarding the diffusive permeability of the membrane were performed with chloride, inulin and vitamin $B_{12}$. The permeabilities of chloride, inulin and vitamin $B_{12}$ were $13.4 \cdot 10^{-4}$ cm/s, $3.1 \cdot 10^{-4}$ cm/s and $2.3 \cdot 10^{-4}$ cm/s, respectively.

The hollow fibers were also used in a cell expansion system based on hollow fibers. After loading of 50 ml one day-old unprocessed human bone marrow in a bioreactor with a surface area of approx. 1 $m^2$, 6,220,000±3,281,331 MSC were harvested after a 13-day expansion period (n=4). The average doubling time was 38±9 hours.

Example 10

Preparation of a Hollow Fiber Membrane

A polymer solution was prepared by dissolving polyethersulfone (Ultrason® 6020, BASF), polyvinylpyrrolidone (K30 and K85, BASF), the polyurethane (Desmopan® PU 9665 DU, Bayer MaterialScience AG) as well as distilled water in N-methylpyrrolidone (NMP). The weight fraction of the different components in the polymer spinning solution, PES/PVP(K85)/PVP(K30)/9665 DU/$H_2O$/NMP was 14/3/5/0.5/3/74.5. The viscosity of the polymer solution was 12,300 mPa·s.

The polymer preparation procedure was kept as described in Example 9, except for the following points:
 Water/NMP wt.-% in the bore liquid: 58/42 wt.-%
 Temperature of the die: 45° C.
 Flow rate washing baths: 80 l/h
 Inlet temperature washing bath: 66° C.

The remaining process steps were as in Example 9. The dried hollow fiber membrane had an inner diameter of 215 μm and an outer diameter of 311 μm and a fully asymmetric membrane structure. The active separation layer of the membrane was at the inner side. The active separation layer was defined as the layer with the smallest pores. Here, filters with an effective surface area of 0.9 m² were produced, packed in special plastic bags and finally dry gamma-sterilized (dose 25 kGy).

After loading of 50 ml one day-old unprocessed human bone marrow in a bioreactor (online-dried) with a surface area of approx. 1 m², 10,043,333±3,785,318 MSC were harvested after a 13-day expansion period (n=4). The average doubling time was 35±4 hours.

Example 11

Comparative

Preparation of a Comparative Hollow Fiber Membrane Without Polyurethane

A polymer solution was prepared by dissolving polyethersulfone (Ultrason® 6020, BASF), polyvinylpyrrolidone (K30 and K85, BASF), polyamide (Trogamid® T) as well as distilled water in N-Methylpyrrolidone (NMP). The weight fraction of the different components in the polymer spinning solution, PES/PVP(K85)/PVP(K30)/Trogamid T/$H_2$O/NMP was 13.55/2/5/0.05/3/74.6. The viscosity of the polymer solution was 5,042 mPa·s.

The polymer preparation procedure was kept as described in Example 9, except for the following point:
Temperature of the die: 55° C.

The remaining process steps were as described in Example 9. The dried hollow fiber membrane had an inner diameter of 215 μm and an outer diameter of 315 μm and a fully asymmetric membrane structure. The active separation layer of the membrane was at the inner side. The active separation layer was defined as the layer with the smallest pores. The hydraulic permeability (Lp value) of the membrane was measured from inside to outside using the method described earlier. The membrane showed a hydraulic permeability of $3 \cdot 10^{-4}$ cm³/(cm² bar sec). A scanning electron micrograph of the cross-section and the inner surface of the membrane are shown in FIG. 13.

Example 12

Long-Term Culture of MSC on Polyurethane-Containing Flat-Sheet Membranes Over Four Passages As it is generally desirable to reuse a given membrane, e.g. within a bioreactor, for several passages when expanding a given cell culture, such as, for example, MSC derived from one host for expansion and re-implantation into the same or another host, the polyurethane-containing membranes of the invention were tested for their ability to support such culture technique. For comparison, the same cells were cultured in parallel on standard TCPS. The membranes of the invention contained, in the polymer solution, 2 wt.%, 0.5 wt.-%, 0.2 wt.-%, 0.1 wt.-%, 0.05 wt.-% and 0.01 wt.-% polyurethane (see Examples 1 to 7). MSC were cultured in alpha-MEM medium, supplemented with 10% FCS, 1% penicillin/streptomycin and 1% ultraglutamine. Cells were cultivated for about 10 days during each passage. After seeding and cultivation for a first 10 days period at 37° C. and 5% $CO_2$, with regular media exchanges after 2 to 3 days, cells were detached from their respective matrix with accutase, a mixture of proteolytic and collagenolytic enzymes from an invertebrate species. Besides trypsin, accutase is used to detach adherent cells from surfaces. First the substrates to which the MSC were attached were washed with a small volume of sterile PBS and wash liquid was removed. This was repeated two times; if necessary. 0.5 ml of accutase were added to one well. The culture was returned to a +37° C. incubator and the cells were allowed to detach for 30 minutes. This step can be repeated, if necessary. Finally, the cells were counted and reseeded on the same substrate material. This was repeated twice, i.e. the cells underwent four passages. The cell counts after each passage show that the membranes of the invention well promote several passages on the same substrate (FIG. 6).

The invention claimed is:
1. A membrane for promoting the adherence of cells without pre-treatment of said membrane or the addition of exogenous factors, the membrane comprising a first polymer which is polyvinylpyrrolidone, a second polymer which is a polyurethane, and a third polymer selected from the group consisting of polysulfone, polyethersulfone and polyarylethersulfone.
2. The membrane of claim 1, wherein the polyurethane is a thermoplastic polyurethane.
3. The membrane of claim 1 further comprising a polyamide.
4. The membrane of claim 1 wherein said membrane is a hollow fiber membrane.
5. The membrane of claim 1 wherein said membrane is a flat sheet membrane.
6. The membrane of claim 2 wherein said membrane is a hollow fiber membrane.
7. The membrane of claim 2 wherein said membrane is a flat sheet membrane.
8. The membrane of claim 2 further comprising a polyamide.
9. The membrane of claim 8 wherein said membrane is a flat sheet membrane.
10. The membrane of claim 3 wherein said membrane is a hollow fiber membrane.
11. The membrane of claim 3 wherein said membrane is a flat sheet membrane.

* * * * *

UNITED STATES PATENT AND TRADEMARK OFFICE
CERTIFICATE OF CORRECTION

PATENT NO. : 8,435,751 B2
APPLICATION NO. : 13/120397
DATED : May 7, 2013
INVENTOR(S) : Zweigart et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 119 days.

Signed and Sealed this
Eighth Day of September, 2015

Michelle K. Lee
*Director of the United States Patent and Trademark Office*